(12) United States Patent
Pankratz et al.

(10) Patent No.: US 7,802,484 B2
(45) Date of Patent: Sep. 28, 2010

(54) COMPACT VIBRATORY FLOWMETER FOR MEASURING FLOW CHARACTERISTICS OF A MULTI-PHASE FLOW MATERIAL

(75) Inventors: Anthony William Pankratz, Arvada, CO (US); Mark James Bell, Arvada, CO (US); Andrew Timothy Patten, Boulder, CO (US)

(73) Assignee: Micro Motion, Inc., Boulder, CO (US)

( * ) Notice: Subject to any disclaimer, the term of this patent is extended or adjusted under 35 U.S.C. 154(b) by 563 days.

(21) Appl. No.: 11/909,503

(22) PCT Filed: Apr. 6, 2005

(86) PCT No.: PCT/US2005/011420
§ 371 (c)(1),
(2), (4) Date: Sep. 24, 2007

(87) PCT Pub. No.: WO2006/107297
PCT Pub. Date: Oct. 12, 2006

(65) Prior Publication Data
US 2010/0083769 A1    Apr. 8, 2010

(51) Int. Cl.
*G01F 1/84* (2006.01)
(52) U.S. Cl. .............................. 73/861.355; 73/861.356; 73/861.357
(58) Field of Classification Search ........................ None
See application file for complete search history.

(56) References Cited

U.S. PATENT DOCUMENTS 3,690,171 A * 9/1972 Tippetts et al. ........... 73/861.19
4,823,614 A   4/1989 Dahlin
4,856,346 A   8/1989 Kane
5,796,011 A   8/1998 Keita et al.

(Continued)

FOREIGN PATENT DOCUMENTS

EP    1260798 A1   11/2002

(Continued)

OTHER PUBLICATIONS

Coriolis Mass Flowmeters [online], retrieved on Mar. 3, 2005, retrieved from Endress & Hauser website on the Internet <URL: http://www.us.endress.com/eh/sc/america/us/en/products/home.nsf/>.

*Primary Examiner*—Harshad Patel
(74) *Attorney, Agent, or Firm*—The Ollila Law Group LLC

(57) ABSTRACT

A compact vibratory flowmeter (200) for measuring flow characteristics of a multi-phase flow material at a flow material pressure of greater than about 10 pounds-per-square-inch (psi) is provided according to an embodiment of the invention. The compact vibratory flowmeter (200) includes one or more flow conduits (301), at least two pickoff sensors (308), and a driver (309). The compact vibratory flowmeter (200) further includes a maximum water drive frequency in the one or more flow conduits (301) that is less than about 250 Hertz (Hz) and an aspect ratio (L/H) of the one or more flow conduits (301) that is greater than about 2.5. A height-to-bore ratio (H/B) of the one or more flow conduits (301) is less than about 10 and a bowed flow conduit geometry includes end bend angles Θ of between about 120 degrees and about 170 degrees.

22 Claims, 7 Drawing Sheets

U.S. PATENT DOCUMENTS

| | | |
|---|---|---|
| 6,308,580 B1 | 10/2001 | Crisfield et al. |
| 6,666,098 B2 | 12/2003 | Drahm et al. |
| 2002/0117010 A1 | 8/2002 | Drahm et al. |
| 2004/0255648 A1 | 12/2004 | Sparks |

FOREIGN PATENT DOCUMENTS

| | | |
|---|---|---|
| JP | 11326004 A | 11/1999 |
| RU | 2237869 C2 | 10/2004 |
| WO | WO-0057141 | 9/2000 |
| WO | WO2004/036207 A2 | 4/2004 |

\* cited by examiner

COMPACT VIBRATORY FLOWMETER FOR MEASURING FLOW CHARACTERISTICS OF A MULTI-PHASE FLOW MATERIAL

BACKGROUND OF THE INVENTION

1. Field of the Invention

The present invention relates to a compact vibratory flowmeter, and more particularly, to a compact vibratory flowmeter for measuring flow characteristics of a multi-phase flow material.

2. Statement of the Problem

Vibrating conduit sensors, such as Coriolis mass flow meters, typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness, and damping characteristics of the containing conduit and the material contained therein.

A typical Coriolis mass flow meter includes one or more conduits that are connected inline in a pipeline or other transport system and convey material, e.g., fluids, slurries and the like, in the system. Each conduit may be viewed as having a set of natural vibration modes including, for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pickoff sensors) are typically employed in order to measure a vibrational response of the flow conduit or conduits, and are typically located at positions upstream and downstream of the actuator. The two pickoff sensors are connected to electronic instrumentation by cabling. The instrumentation receives signals from the two pickoff sensors and processes the signals in order to derive a mass flow rate measurement.

One difficulty in using a flowmeter to measure a flow material is when the flow material is non-uniform, such as in a multi-phase flow condition. In a multi-phase flow condition, the flow material includes two or more of a gas phase, a liquid phase, and a solid phase. For example, a common flow measurement scenario is where the flow material includes gas entrained in a liquid. Air is a commonly entrained gas. Because gas is compressible, the properties of the flow material can vary and therefore the entrained gas can cause erroneous readings in the flowmeter. Entrained gas can degrade the accuracy of mass flow rate and density measurements, and therefore can indirectly affect a volume measurement.

FIG. 1 shows a U-shaped vibratory flowmeter of the prior art. This prior art U-shaped vibratory flowmeter has a very low aspect ratio, where the aspect ratio comprises a meter overall length (L) divided by a meter overall height (H), i.e., the aspect ratio=L/H. It can be seen from this figure that the prior art aspect ratio is typically much less than one, especially for a prior art U-shaped flowmeter. In applications where the conduit diameter is large, it can be seen that the small aspect ratio of this prior art flowmeter will require a large amount of vertical physical space for installation.

In many settings, the physical space that is available for a flowmeter is limited. For example, both the meter overall length (L) and the meter overall height (H) may be dictated by the available installation space. Consequently, there is a need for a compact flowmeter that features both a reduced length (L) and a reduced height (H), and a high aspect ratio (L/H) (i.e., is compact). Furthermore, there is an increasing demand for smaller, more compact flowmeters that can provide a needed measurement capability and a high level of measurement accuracy and reliability.

In the prior art, attempts to produce a compact vibratory flowmeter have comprised scaling down existing flowmeters for such applications and/or using bowed or straight flow conduits. However, this has been met with unexpected complications and with unsatisfactory flowmeter accuracy. One result of scaling down an existing flowmeter design is that the stiffness of a flow conduit can increase by a large amount. This increased stiffness characteristic results in an increase in the drive frequency of the flowmeter. Problematically, this relatively high drive frequency results in a degraded performance and/or accuracy for multi-phase flow materials. When gas is entrained in the flow material (such as air bubbles, for example), the flow material resonant frequency is affected and is lower than a resonant frequency of a pure fluid flow material. As a result, a drive frequency employed by a prior art flowmeter may be at or near a flow material resonant frequency. It has been found through research that the accuracy of a flowmeter decreases as the flow material resonant frequency of a multi-phase flow approaches the drive frequency of the flowmeter. Consequently, the entrained gas results in an inability of the flowmeter to accurately measure flow characteristics of the flow material and to measure non-flow characteristics.

SUMMARY OF THE SOLUTION

The above and other problems are solved and an advance in the art is achieved through the provision of a compact vibratory flowmeter for measuring flow characteristics of a multi-phase flow material.

A compact vibratory flowmeter for measuring flow characteristics of a multi-phase flow material at a flow material pressure of greater than about 10 pounds-per-square-inch (psi) is provided according to an embodiment of the invention. The compact vibratory flowmeter comprises one or more flow conduits, at least two pickoff sensors affixed to the one or more flow conduits, and a driver configured to vibrate the one or more flow conduits. The compact vibratory flowmeter further comprises a maximum water drive frequency in the one or more flow conduits that is less than about 250 Hertz (Hz). The compact vibratory flowmeter further comprises an aspect ratio (L/H) of the one or more flow conduits that is greater than about 2.5 and a height-to-bore ratio (H/B) of the one or more flow conduits that is less than about 10. The compact vibratory flowmeter further comprises a bowed flow conduit geometry in the one or more flow conduits that includes end bend angles θ of between about 120 degrees and about 170 degrees.

A method for constructing a compact vibratory flowmeter for measuring flow characteristics of a multi-phase flow material at a flow material pressure of greater than about 10 pounds-per-square-inch (psi) is provided according to an embodiment of the invention. The method comprises providing one or more flow conduits, providing at least two pickoff sensors affixed to the one or more flow conduits, and providing a driver configured to vibrate the one or more flow conduits. The method further comprises providing a maximum water drive frequency that is less than about 250 Hertz (Hz), providing an aspect ratio (L/H) of the one or more flow conduits that is greater than about 2.5, and providing a height-to-bore ratio (H/B) of the one or more flow conduits that is less than about 10. The method further comprises providing a bowed flow conduit geometry in the one or more flow conduits that includes end bend angles θ of between about 120 degrees and about 170 degrees.

A method for constructing a compact vibratory flowmeter for measuring flow characteristics of a multi-phase flow material at a flow material pressure of greater than about 10 pounds-per-square-inch (psi) is provided according to an embodiment of the invention. The method comprises providing one or more flow conduits, providing at least two pickoff sensors affixed to the one or more flow conduits, and providing a driver configured to vibrate the one or more flow conduits. The method further comprises providing a predetermined pressure drop in the one or more flow conduits and providing a predetermined pressure rating in the one or more flow conduits. The method further comprises providing an aspect ratio (L/H) of the one or more flow conduits that is greater than about 2.5 and providing a height-to-bore ratio (H/B) that is less than about 10. The method further comprises providing end bend angles θ between about 120 degrees to about 170 degrees in the one or more flow conduits and providing a maximum water drive frequency that is less than about 250 Hertz (Hz).

ASPECTS OF THE INVENTION

In one aspect of the compact vibratory flowmeter, the maximum water drive frequency is less than about 200 Hz.

In another aspect of the compact vibratory flowmeter, the maximum water drive frequency is based on an effective length $L_E$ of the one or more flow conduits, a moment of inertia (I) of the one or more flow conduits, one or more balance masses affixed to the one or more flow conduits, and the conduit geometry of the one or more flow conduits.

In yet another aspect of the compact vibratory flowmeter, the maximum water drive frequency is based on a predetermined minimum acceptable density accuracy of the compact vibratory flowmeter for a multi-phase flow material.

In yet another aspect of the compact vibratory flowmeter, the one or more flow conduits comprise one or more substantially self-draining flow conduits.

In yet another aspect of the compact vibratory flowmeter, the compact vibratory flowmeter further comprises a predetermined pressure drop in the one or more flow conduits.

In yet another aspect of the compact vibratory flowmeter, the compact vibratory flowmeter further comprises a predetermined pressure drop in the one or more flow conduits that is based on a predetermined total flow path length $L_T$, a predetermined meter friction factor (f), a predetermined conduit inner diameter (ID), a predetermined fluid density ($\rho_f$), and a predetermined flow velocity (V).

In yet another aspect of the compact vibratory flowmeter, the compact vibratory flowmeter further comprises a predetermined pressure rating in the one or more flow conduits.

In one aspect of the method, the maximum water drive frequency is less than about 200 Hz.

In another aspect of the method, the method further comprises determining the maximum water drive frequency based on an effective length $L_E$ of the one or more flow conduits, a moment of inertia (I) of the one or more flow conduits, one or more balance masses affixed to the one or more flow conduits, and the conduit geometry of the one or more flow conduits.

In yet another aspect of the method, the method further comprises determining the maximum water drive frequency based on a predetermined minimum acceptable density accuracy of the compact vibratory flowmeter for a multi-phase flow material.

In yet another aspect of the method, the one or more flow conduits comprise one or more substantially self-draining flow conduits.

In yet another aspect of the method, the method further comprises providing a predetermined pressure drop in the one or more flow conduits.

In yet another aspect of the method, the method further comprises providing a predetermined pressure drop in the one or more flow conduits that is based on a predetermined total flow path length $L_T$, a predetermined meter friction factor (f), a predetermined conduit inner diameter (ID), a predetermined fluid density ($\rho_f$), and a predetermined flow velocity (V).

In yet another aspect of the method, the method further comprises providing a predetermined pressure rating in the one or more flow conduits.

DESCRIPTION OF THE DRAWINGS

The same reference number represents the same element on all drawings.

DETAILED DESCRIPTION OF THE INVENTION

FIGS. 2-7 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 2:
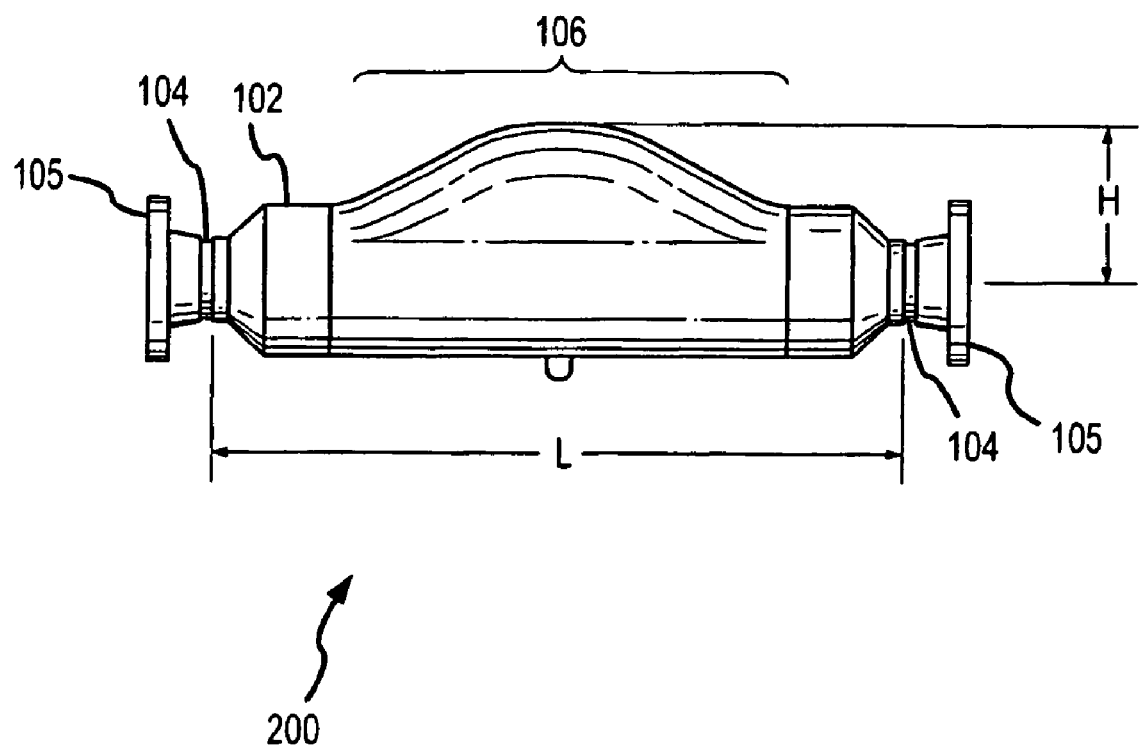
FIG. 2 shows a compact vibratory flowmeter according to an embodiment of the invention.

FIG. 2 shows a compact vibratory flowmeter 200 according to an embodiment of the invention. The compact vibratory flowmeter 200 includes manifolds 104, flanges 105, a casing 102, and a conduit portion 106. The compact vibratory flowmeter 200 includes one or more flow conduits 301 (see FIG. 3) as part of the conduit portion 106 inside the casing 102. In some embodiments, the compact vibratory flowmeter 200 can include two flow conduits 301. The one or more flow conduits 301 can comprise bowed flow conduits.

The compact vibratory flowmeter 200 in one embodiment comprises a Coriolis flowmeter. In another embodiment, the compact vibratory flowmeter 200 comprises a vibrating densitometer.

The compact vibratory flowmeter 200 can be designed to achieve a desired minimum measurement accuracy. The compact vibratory flowmeter 200 can be designed to achieve a minimum density measurement accuracy. The compact vibratory flowmeter 200 can be designed to achieve a minimum density measurement accuracy for a multi-phase flow material. The compact vibratory flowmeter 200 can measure both flow and non-flow characteristics of the flow material.

Many factors can affect the operation (and therefore accuracy) of a vibratory flowmeter. Three of the most important factors that affect operation are a drive frequency that is used to vibrate the one or more flow conduits, a flow material pressure, and a flow conduit geometry. Proper design of a compact vibratory flowmeter can generally be accomplished through appropriate selection of these three factors, even for use with a multi-phase flow material.

A compact vibratory flowmeter according to the invention includes a drive frequency of less than about 250 Hertz (Hz) on any fluid that includes water, such as a cement flow material, for example. In some embodiments, the drive frequency is less than about 200 Hz. The drive frequency can be based on an effective length $L_E$ of the one or more flow conduits 301, a moment of inertia (I) of the one or more flow conduits 301, and the geometry of the one or more flow conduits 301. In addition, the drive frequency can be further affected by one or more balance masses that can optionally be affixed to the one or more flow conduits 301, as needed. The effective length $L_E$ can depend on the flow conduit geometry. The flow conduit wall thickness can depend on the flow material pressure. The moment of inertia (I) can depend on the flow conduit inner diameter and the flow conduit wall thickness, among other things. In addition, the drive frequency can be based on a predetermined minimum acceptable density accuracy (see FIG. 4 and the accompanying discussion).

A compact vibratory flowmeter according to the invention includes a flow material pressure that is greater than about 10 pounds-per-square-inch (psi). In some embodiments, the flow material pressure is between about 10 psi and about 475 psi. In some embodiments, the flow material pressure is greater than about 15 psi. The flow material pressure can be selected according to a desired application or can be specified by an end user.

A compact vibratory flowmeter according to the invention includes a predetermined compact geometry. The predetermined compact geometry can include one or more of a predetermined aspect ratio (L/H), a predetermined height-to-bore ratio (H/B), or a bowed flow conduit geometry. The predetermined aspect ratio (L/H) is greater than about 2.5. The predetermined height-to-bore ratio (H/B) is less than about 10. The bowed flow conduit geometry can include end bend angles Θ of between 120 degrees and about 170 degrees. The bowed flow conduit geometry can be substantially self-draining.

The compact vibratory flowmeter 200 can further include a predetermined pressure drop (ΔP) in the one or more flow conduits 301. The predetermined pressure drop (ΔP) can be based on a predetermined total flow path length $L_T$ (see FIG. 3), a predetermined meter friction factor (f), a predetermined conduit inner diameter (ID), a predetermined fluid density ($\rho_f$), and a predetermined flow velocity (V). In one embodiment, the predetermined pressure drop (ΔP) can be calculated according to the formula:

$$\Delta P = \frac{\rho V^2}{2} \left[ \frac{fL_T}{ID} \right] \quad (1)$$

The compact vibratory flowmeter 200 can further include a predetermined pressure rating in the one or more flow conduits 301. The predetermined pressure rating can be selected according to a particular application or by an end user.

The compact vibratory flowmeter 200 in some embodiments is constructed to have a high aspect ratio. In one embodiment, the meter overall length (L) is substantially the distance between manifolds 104 of the flowmeter (see FIG. 2), while the meter overall height (H) is substantially the distance between a centerline of the inlet/outlet manifolds and the farthest away centerline (i.e., the center of the peak of the bowed portion). The aspect ratio is therefore an approximate quantification of the overall shape and size of the flowmeter. A high aspect ratio (L/H) connotes that the flowmeter has a low height compared to its length. Therefore, the compact vibratory flowmeter 200 according to the invention is relatively small and therefore easy to accommodate in most metering applications. The high aspect ratio enables the compact vibratory flowmeter 200 to be installed in small spaces. The high aspect ratio enables the compact vibratory flowmeter 200 to be used in more applications. In one embodiment, the compact vibratory flowmeter 200 can be used in a cement casing operation, including in machinery for mixing and/or pumping liquid cement. Other uses and other flow materials are contemplated and are within the scope of the description and claims.

The height-to-bore ratio (H/B) comprises a ratio of the height (defined above) to an inner diameter of an inlet/outlet manifold. The height-to-bore ratio (H/B) reflects the relationship between vertical height of the compact vibratory flowmeter to the inlet/outlet bores and therefore a flow conduit size. The bore therefore influences the flow velocity (V) and the meter friction factor (f) for a given flow material pressure. In a single flow conduit flowmeter, the bore (B) generally is the same diameter as the flow conduit. However, the bore does not have to be the same as the inside diameter of a flow conduit.

The compact vibratory flowmeter 200 features a low drive frequency for a flow material, including for a cement flow material, for example. This low drive frequency is achieved even while achieving a high aspect ratio and therefore a compact overall design. In the prior art, a design engineer could choose from either a low drive frequency flowmeter design or a compact flowmeter design, but not both.

The drive frequency is the frequency at which the one or more flow conduits 301 are vibrated in order to measure flow characteristics of the flow material. The drive frequency is typically selected to be at or below a flow material resonant frequency. Therefore, the drive frequency can vary according to the makeup of the flow material. In addition, the drive frequency is affected by the stiffness characteristic of the flowmeter. As the stiffness characteristic increases, the drive frequency also typically increases. The basic difficulty in providing a compact flowmeter featuring a low drive frequency is that reductions in aspect ratio/overall size increase the stiffness characteristic. For example, one design feature is the meter overall length (L). Without any other changes being made to a flowmeter, the stiffness characteristic increases as the meter overall length (L) decreases. Another design feature that affects the stiffness characteristic is the effective length $L_E$ of a vibrating portion of a flow conduit 301 (see FIG. 3).

Figure 1:
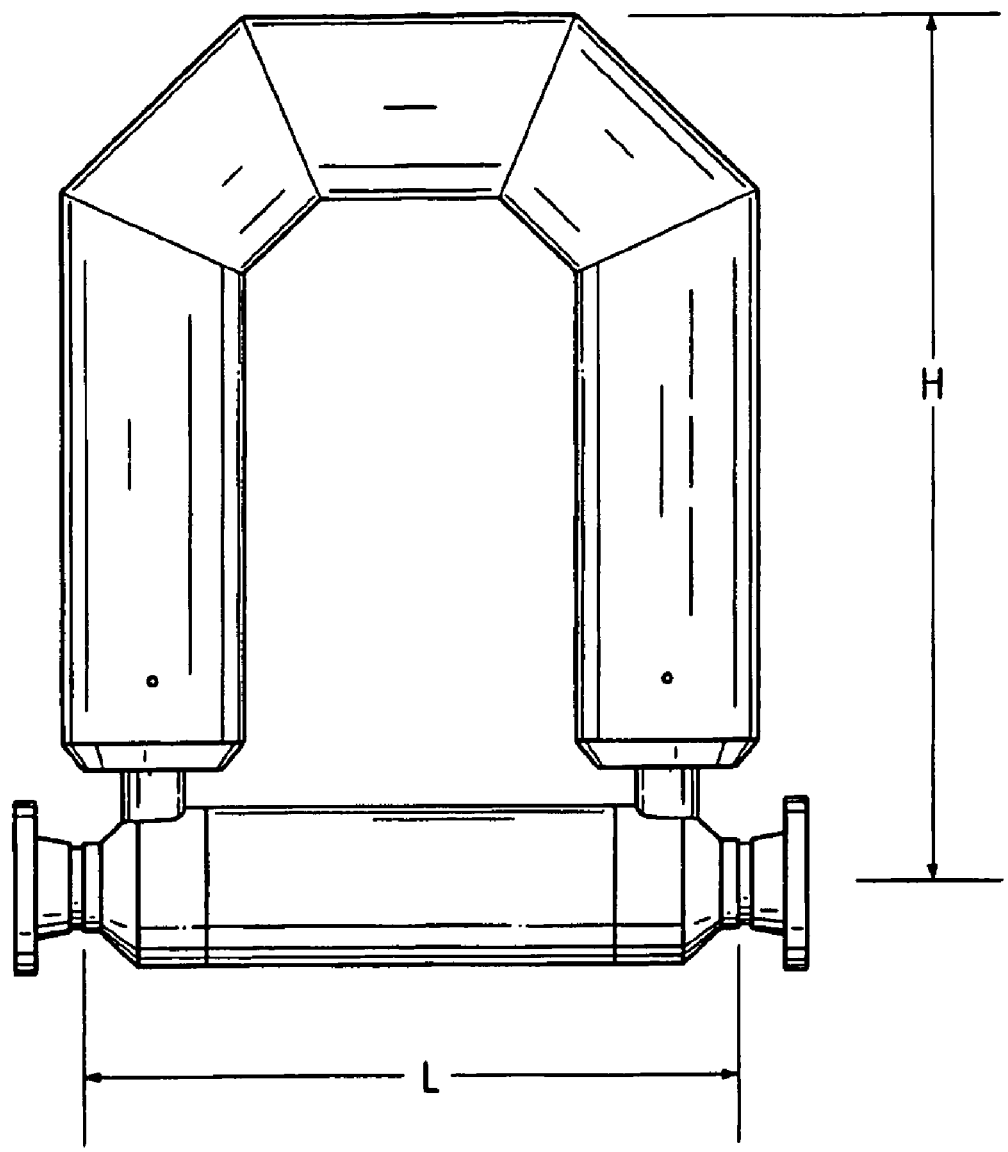
FIG. 1 shows a U-shaped vibratory flowmeter of the prior art.

The effective length $L_E$ is less than the total flow path length $L_T$ for a straight or bowed conduit flowmeter. The effective length $L_E$ can be shortened by shortening the total flow path length $L_T$ or by the addition of brace bars, brackets, etc., that restrict the ends of the flow conduits. In addition, the effective length $L_E$ can be shortened by changes in the configuration of a flowmeter. For example, a U-shaped flowtube has a much greater effective length $L_E$ than a straight conduit flowmeter (see FIGS. 1 and 3). As a result, by shifting to a straight flow conduit or a moderately bowed flow conduit, the stiffness characteristic and the drive frequency of the flowmeter will be greatly increased.

The flowmeter according to the embodiments of the invention is not merely a scaled-down prior art flowmeter. The flowmeter according to the embodiments of the invention is designed so that the drive frequency is less, or even much less, than the flow material resonant frequency. Ideally, the meter drive frequency should be a discernable distance from the flow material resonant frequency. As a result, the flowmeter according to the embodiments of the invention provides a low-profile, self-draining, compact vibratory flowmeter while yet achieving a desired measurement accuracy, even in the presence of varying amounts of entrained gas.

Figure 3:
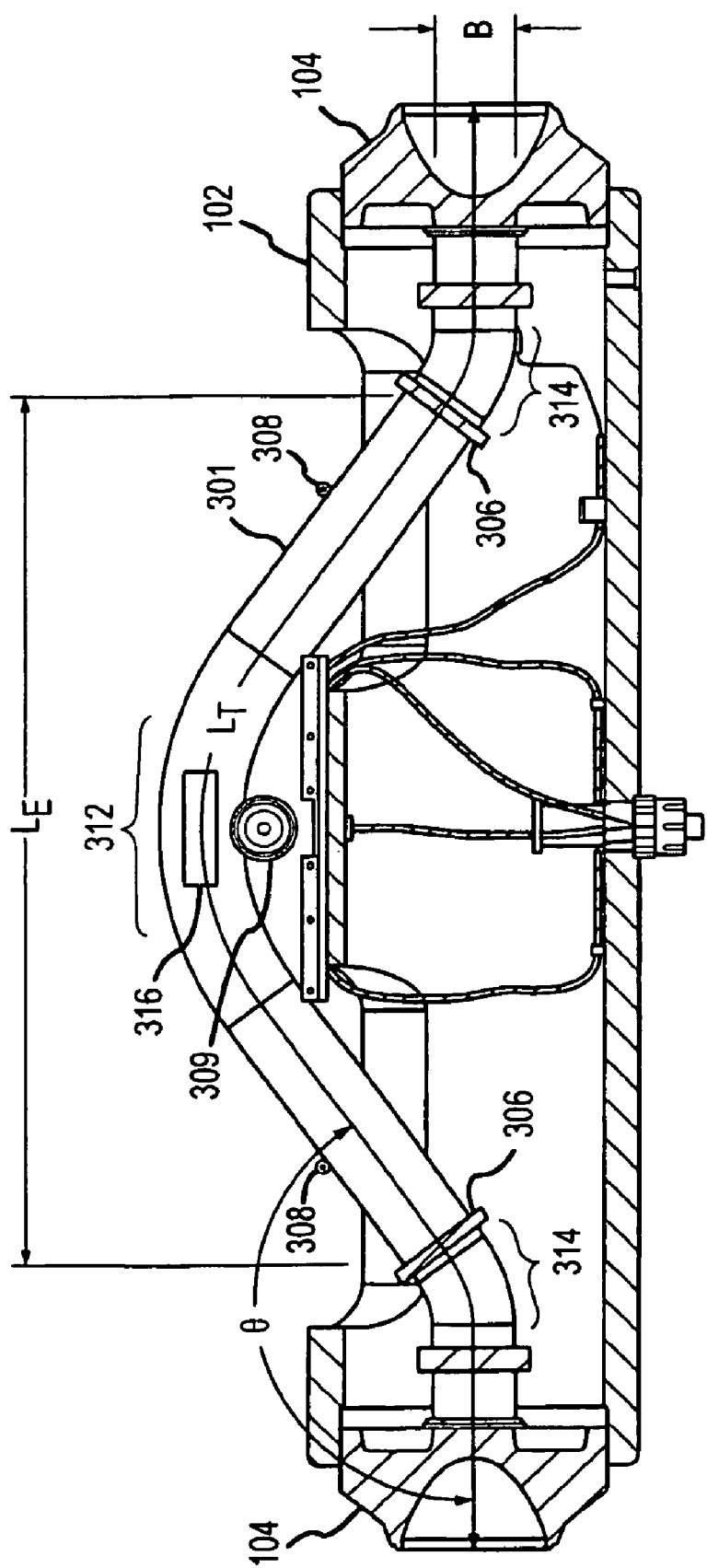
FIG. 3 shows components of the compact vibratory flowmeter according to an embodiment of the invention.

FIG. 3 shows components of the compact vibratory flowmeter 200 according to an embodiment of the invention. The compact vibratory flowmeter 200 includes, in addition to the components shown and discussed in FIG. 2, one or more flow conduits 301, brace bars 306, pickoff sensors 308, and a driver 309. Other components can also be included, such as pick-off sensors, temperature and/or pressure sensors, meter electronics, mass balances 316 as needed, etc.

The flow conduits 301 comprise bowed flow conduits and include a bowed portion formed from at least two end bend portions 314 and a central bend portion 312. The two end bend portions 314 each comprise end bend angles $\Theta$ between about 120 degrees to about 170 degrees. In the embodiment shown, the end bend angles $\Theta$ comprise bends of about 145 degrees. The bowed portion can increase the effective length $L_E$, as smaller end bend angles $\Theta$ can make the flow conduits more U-shaped and therefore can increase the effective length $L_E$.

The compact vibratory flowmeter 200 can include brace bars 306. The brace bars 306 are employed to anchor the ends of the flow conduit 301. In an embodiment that includes two flow conduits 301, the brace bars 306 can additionally affix the flow conduits 301 to each other. The brace bars 306 can set an effective length $L_E$ of the flowmeter 200. Because the effective length $L_E$ can affect a stiffness characteristic of the compact vibratory flowmeter 200, the effective length $L_E$ is modified in order to achieve the desired drive frequency. In some embodiments, the brace bars 306 are installed as far apart as possible in order to reduce the drive frequency of the compact vibratory flowmeter 200, while maintaining a desirable meter modal separation/performance. Alternatively, in some embodiments the brace bars 306 are left out in order to maximize the effective length $L_E$.

Another characteristic that can affect the operation of the compact vibratory flowmeter 200 is the internal bore (B) of the one or more flow conduits 301 (see FIG. 3). The bore is the inside diameter of the inlets and outlets of the compact vibratory flowmeter 200, such as at the manifolds 104. The cross-sectional area of the bore in one embodiment is substantially equal to the cross-sectional area(s) of the flow conduit(s). A height-to-bore ratio therefore is an indicator of the amount of bow in the flowmeter per cross-sectional area. In one embodiment of the invention, the height-to-bore ratio (H/B) is less than about 10.

Another characteristic that can affect the operation of the compact vibratory flowmeter 200 is the added presence of balance weights 316 attached to the one or more flow conduits 301. Added balance weights 316 affect the overall mass of the flow conduits 301 while not substantially affecting a stiffness characteristic. Therefore, the balance weights 316 can affect the drive frequency. Increasing the mass of the flow conduits 301 reduces the drive frequency.

Yet another characteristic that can affect the operation of the compact vibratory flowmeter 200 is the wall thickness of the flow conduits 301. Wall thickness is generally chosen to accommodate the pressure of the flow material. However, a thicker conduit wall will increase the stiffness characteristic of the flow conduit 301. Therefore, in the compact vibratory flowmeter 200 according to the invention, the wall thickness is chosen to be relatively thin in order to achieve a lower drive frequency. This is possible where the flow material is not at a high pressure.

Figure 4:
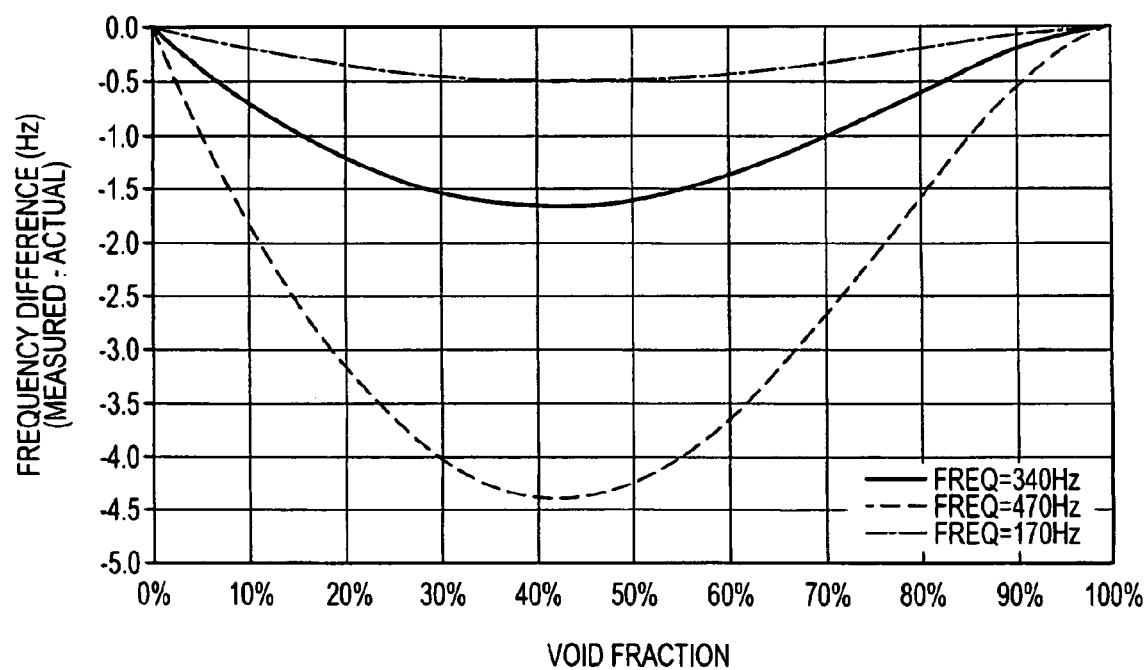
FIG. 4 is a graph of frequency difference (i.e., frequency error) of actual frequency versus measured frequency over a range of void fractions.

FIG. 4 is a graph of frequency difference (i.e., frequency error) of actual frequency versus measured frequency over a range of void fractions. The graph represents measured values of a cement flow material at a pressure of 15 psi. The lower line comprises plotted frequency values for a prior art flowmeter operating at a drive frequency of 470 Hz. The middle line comprises plotted frequency values for a prior art flowmeter operating at a drive frequency of 340 Hz. In contrast, the upper line comprises plotted frequency values of the drive frequency of the compact vibratory flowmeter according to the invention, wherein the compact vibratory flowmeter according to the invention is operating a drive frequency of about 170 Hz. Each of the frequency responses is from a flowmeter having the same flow conduit geometry and differing only in terms of effective length $L_E$ and conduit wall thickness. It can be seen from the graph that the 170 Hz flowmeter drive frequency deviates from an actual response by no more than 0.5 Hz for any value of void fraction. Therefore, a compact vibratory flowmeter operating at a frequency below 250 Hz provides a high level of accuracy in frequency measurements. It can be seen from this graph that a desired level of frequency accuracy can be achieved, at least in part, by selecting an appropriately low operating frequency.

Figure 5:
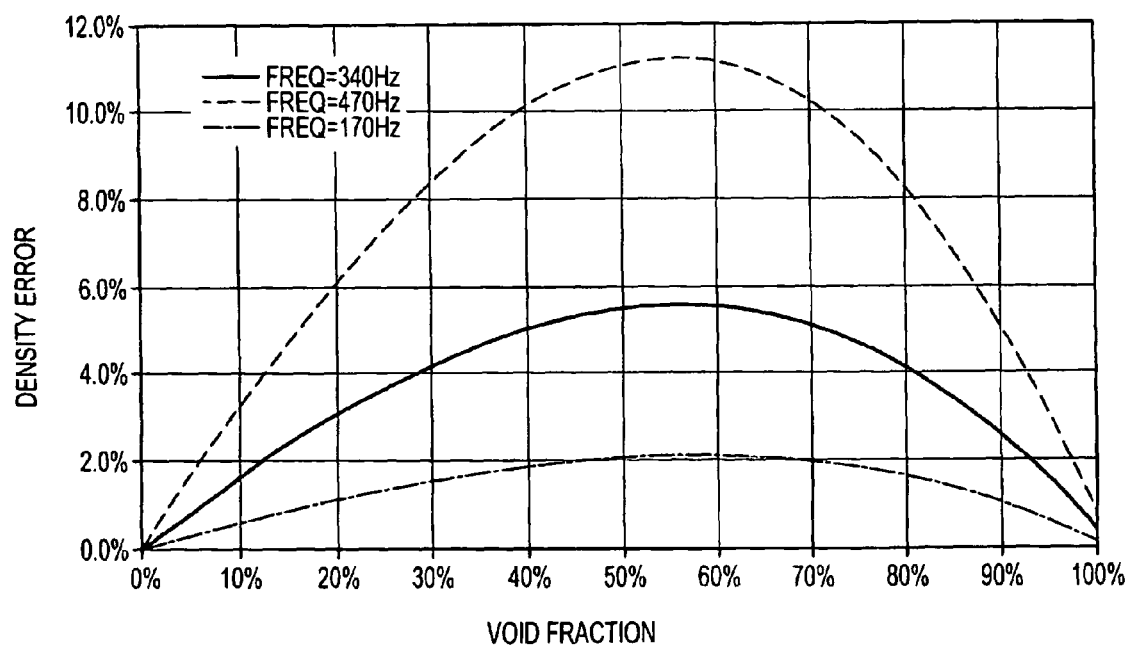
FIG. 5 is a graph of density error over a range of void fractions.

FIG. 5 is a graph of density error over a range of void fractions. The density error graph is a complement to the frequency difference graph, as density is approximately equal to 1 over frequency squared ($\rho=1/f^2$). The top line comprises plotted density values for a prior art flowmeter operating at a drive frequency of 470 Hz. The middle line comprises plotted density values for a prior art flowmeter operating at a drive frequency of 340 Hz. In contrast, the lower line comprises plotted density values of a compact vibratory flowmeter according to the invention, wherein the compact vibratory flowmeter according to the invention is operating a drive frequency of 170 Hz. It can be seen from the graph that the density values measured by the 170 Hz flowmeter deviate from actual densities by no more than about 2.1 percent for any value of void fraction. Therefore, a compact vibratory flowmeter operating at a frequency below 250 Hz provides a high level of accuracy in density measurements.

Figure 6A:
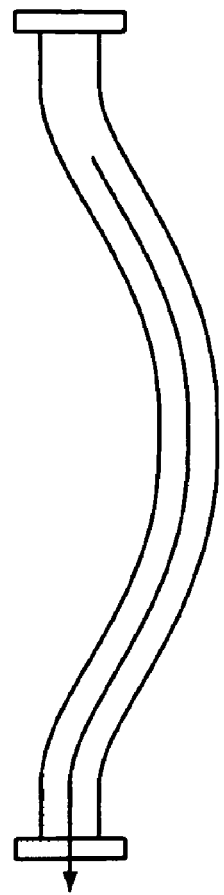
FIGS. 6A-6B show a self-draining aspect of the compact vibratory flowmeter.
Figure 6B:
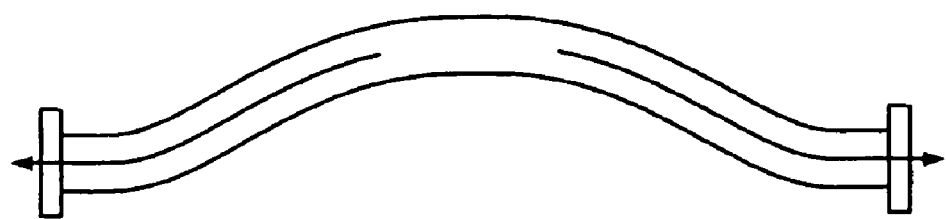

FIGS. 6A-6B show a self-draining aspect of the compact vibratory flowmeter 200. In FIG. 6A, the flow conduit(s) 301 are vertically oriented. Because the flow conduit(s) 301 features a bowed configuration, including end bend angles $\Theta$ greater than 120 degrees, any flow material in the flow conduit(s) 301 will drain out due to gravity (see arrow). Likewise, in FIG. 6B, even when the flow conduit(s) 301 is installed in a horizontal orientation, the flow material will drain out of the flow conduit(s) 301 (see two arrows). This self-draining aspect of the compact vibratory flowmeter 200 is a large improvement over U-shaped flowmeters, as the flow material (such as a cement flow material, for example), will quickly build up on the inside of the flow conduit(s) 301 if it is not self-draining.

Figure 7:
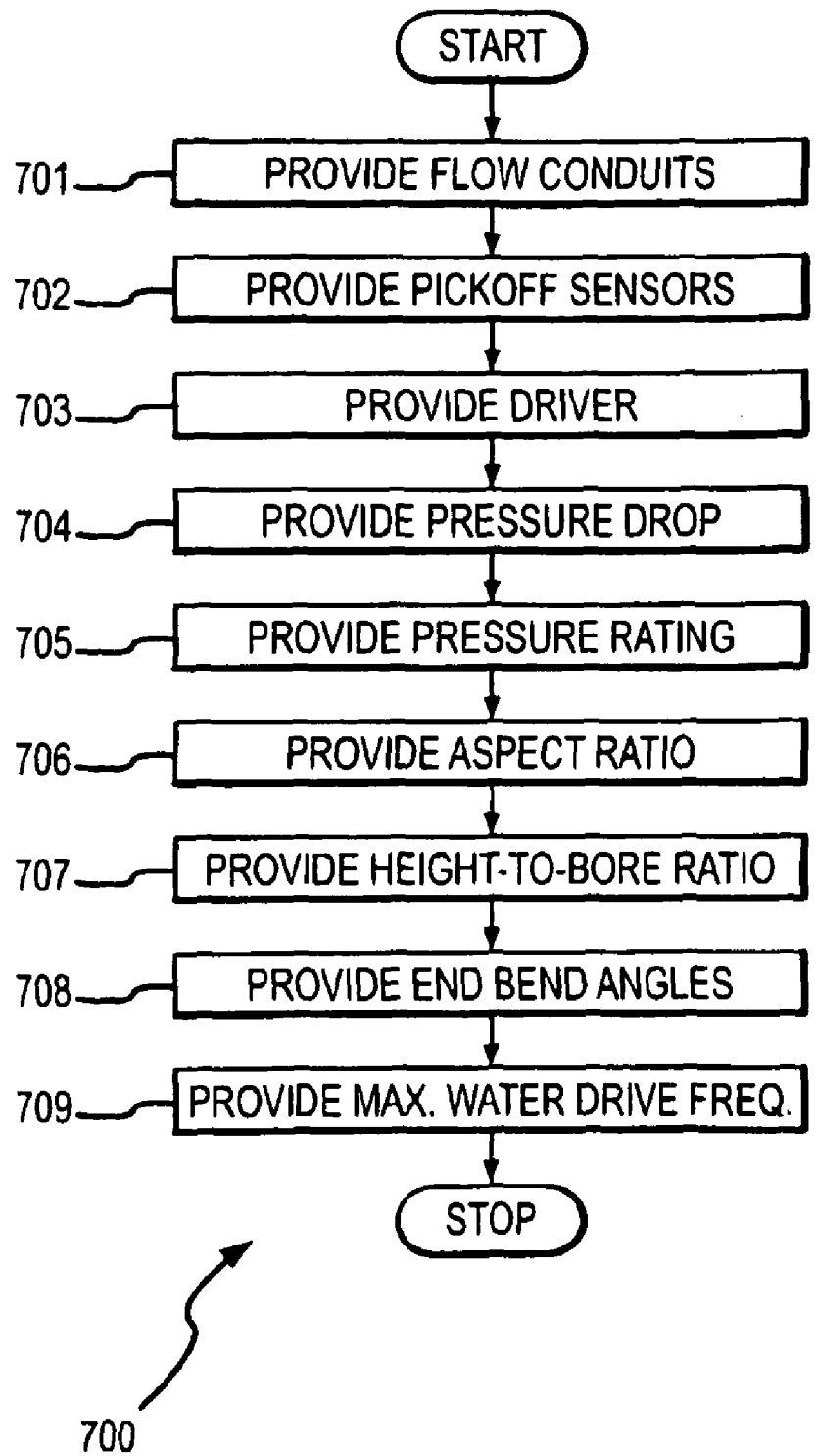
FIG. 7 is a flowchart of a method for constructing a compact vibratory flowmeter for measuring flow characteristics of a multi-phase flow material according to an embodiment of the invention.

FIG. 7 is a flowchart 700 of a method for constructing a compact vibratory flowmeter for measuring flow characteristics of a multi-phase flow material according to an embodiment of the invention. In step 701, a pressure drop is provided in the compact vibratory flowmeter, as previously discussed. The pressure drop can be chosen for a desired application or can be specified by an end user.

In one embodiment, the pressure drop can be determined using several meter factors. For example, the pressure drop (ΔP) can be calculated according to equation (1). Given a fluid density value and an acceptable meter pressure drop (ΔP), the inner diameter (ID) of the one or more flow conduits and the total flow path length $L_T$ can be determined from the equation.

In step 702, a predetermined compact geometry is provided, as previously discussed.

In step 703, a predetermined pressure rating is provided in the compact vibratory flowmeter. The predetermined pressure rating can specify an acceptable upper pressure limit for the compact vibratory flowmeter. In addition, the predetermined pressure rating can influence the wall thickness of the flow conduit(s).

In step 704, predetermined end bend angles Θ are provided in the compact vibratory flowmeter, as previously discussed. The end bend angles Θ can vary according to a flow conduit geometry and according to a desired flow conduit effective length $L_E$. The end bend angles Θ in the compact vibratory flowmeter according to the invention range from about 120 degrees to about 170 degrees. The end bend angles Θ create the bowed shape of the flow conduit(s).

In step 705, a drive frequency is provided in the compact vibratory flowmeter. The drive frequency is less than about 250 Hz. In some embodiments, the drive frequency is less than about 200 Hz. The drive frequency can be determined as a function of other flowmeter parameters, as previously discussed.

The compact vibratory flowmeter according to the invention can be employed according to any of the embodiments in order to provide several advantages, if desired. The invention provides a compact vibratory flowmeter that features a low profile and a high aspect ratio. The invention provides a compact vibratory flowmeter that advantageously offers a low maximum water drive frequency. The invention provides a compact vibratory flowmeter that advantageously offers a low maximum drive frequency that is much less than a drive frequency of a prior art flowmeter of a same overall size and profile.

We claim:

1. A compact vibratory flowmeter (200) for measuring flow characteristics of a multi-phase flow material at a flow material pressure of greater than about 10 pounds-per-square-inch (psi), the compact vibratory flowmeter (200) comprising one or more flow conduits (301), at least two pickoff sensors (308) affixed to the one or more flow conduits (301), and a driver (309) configured to vibrate the one or more flow conduits (301), with the compact vibratory flowmeter (200) being characterized by:
    a maximum water drive frequency in the one or more flow conduits (301) that is less than about 250 Hertz (Hz);
    an aspect ratio (L/H) of the one or more flow conduits (301) that is greater than about 2.5;
    a height-to-bore ratio (H/B) of the one or more flow conduits (301) that is less than about 10; and
    a bowed flow conduit geometry in the one or more flow conduits (301) that includes end bend angles θ of between about 120 degrees and about 170 degrees.

2. The compact vibratory flowmeter (200) of claim 1, wherein the maximum water drive frequency is less than about 200 Hz.

3. The compact vibratory flowmeter (200) of claim 1, with the maximum water drive frequency being based on an effective length $L_E$ of the one or more flow conduits (301), a moment of inertia (I) of the one or more flow conduits (301), one or more balance masses affixed to the one or more flow conduits (301), and the conduit geometry of the one or more flow conduits (301).

4. The compact vibratory flowmeter (200) of claim 1, with the maximum water drive frequency being based on a predetermined minimum acceptable density accuracy of the compact vibratory flowmeter (200) for a multi-phase flow material.

5. The compact vibratory flowmeter (200) of claim 1, with the one or more flow conduits (301) comprising one or more substantially self-draining flow conduits.

6. The compact vibratory flowmeter (200) of claim 1, further comprising a predetermined pressure drop in the one or more flow conduits (301).

7. The compact vibratory flowmeter (200) of claim 1, further comprising a predetermined pressure drop in the one or more flow conduits (301) that is based on a predetermined total flow path length $L_T$, a predetermined meter friction factor (f), a predetermined conduit inner diameter (ID), a predetermined fluid density ($\rho_f$), and a predetermined flow velocity (V).

8. The compact vibratory flowmeter (200) of claim 1, further comprising a predetermined pressure rating in the one or more flow conduits (301).

9. A method for constructing a compact vibratory flowmeter for measuring flow characteristics of a multi-phase flow material at a flow material pressure of greater than about 10 pounds-per-square-inch (psi), the method comprising providing one or more flow conduits, providing at least two pickoff sensors affixed to the one or more flow conduits, and providing a driver configured to vibrate the one or more flow conduits, with the method being characterized by:
    providing a maximum water drive frequency that is less than about 250 Hertz (Hz);
    providing an aspect ratio (L/H) of the one or more flow conduits that is greater than about 2.5;
    providing a height-to-bore ratio (H/B) of the one or more flow conduits that is less than about 10; and
    providing a bowed flow conduit geometry in the one or more flow conduits that includes end bend angles θ of between about 120 degrees and about 170 degrees.

10. The method of claim 9, wherein the maximum water drive frequency is less than about 200 Hz.

11. The method of claim 9, further comprising determining the maximum water drive frequency based on an effective length $L_E$ of the one or more flow conduits, a moment of inertia (I) of the one or more flow conduits, one or more balance masses affixed to the one or more flow conduits, and the conduit geometry of the one or more flow conduits.

12. The method of claim 9, further comprising determining the maximum water drive frequency based on a predetermined minimum acceptable density accuracy of the compact vibratory flowmeter for a multi-phase flow material.

13. The method of claim 9, with the one or more flow conduits comprising one or more substantially self-draining flow conduits.

14. The method of claim 9, further comprising providing a predetermined pressure drop in the one or more flow conduits.

15. The method of claim 9, further comprising providing a predetermined pressure drop in the one or more flow conduits that is based on a predetermined total flow path length $L_T$, a predetermined meter friction factor (f), a predetermined conduit inner diameter (ID), a predetermined fluid density ($\rho_f$), and a predetermined flow velocity (V).

16. The method of claim 9, further comprising providing a predetermined pressure rating in the one or more flow conduits.

17. A method for constructing a compact vibratory flowmeter for measuring flow characteristics of a multi-phase flow material at a flow material pressure of greater than about 10 pounds-per-square-inch (psi), the method comprising providing one or more flow conduits, providing at least two pickoff sensors affixed to the one or more flow conduits, providing a driver configured to vibrate the one or more flow conduits, with the method being characterized by:
   providing a predetermined pressure drop in the one or more flow conduits;
   providing a predetermined pressure rating in the one or more flow conduits;
   providing an aspect ratio (L/H) of the one or more flow conduits that is greater than about 2.5;
   providing a height-to-bore ratio (H/B) of the one or more flow conduits that is less than about 10;
   providing end bend angles θ between about 120 degrees to about 170 degrees in the one or more flow conduits; and
   providing a maximum water drive frequency in the one or more flow conduits that is less than about 250 Hertz (Hz).

18. The method of claim 17, wherein the maximum water drive frequency is less than about 200 Hz.

19. The method of claim 17, further comprising determining the maximum water drive frequency based on an effective length $L_E$ of the one or more flow conduits, a moment of inertia (I) of the one or more flow conduits, one or more balance masses affixed to the one or more flow conduits, and the conduit geometry of the one or more flow conduits.

20. The method of claim 17, further comprising determining the maximum water drive frequency based on a predetermined minimum acceptable density accuracy of the compact vibratory flowmeter for a multi-phase flow material.

21. The method of claim 17, with the one or more flow conduits comprising one or more substantially self-draining flow conduits.

22. The method of claim 17, with the predetermined pressure drop being based on a predetermined total flow path length $L_T$, a predetermined meter friction factor (f), a predetermined conduit inner diameter (ID), a predetermined fluid density ($\rho_f$), and a predetermined flow velocity (V).

* * * * *